United States Patent
Tobe et al.

(10) Patent No.: US 8,194,942 B2
(45) Date of Patent: Jun. 5, 2012

(54) AUTHENTICATION DEVICE AND AUTHENTICATION METHOD

(75) Inventors: Takeo Tobe, Tokorozawa (JP); Kenzo Mizuno, Gunma (JP); Tetsuji Tsuji, Koshigaya (JP); Isao Watanabe, Tokyo (JP); Isao Kikuchi, Higashimurayama (JP); Tadahito Watakai, Honjou (JP)

(73) Assignee: Fit Design System Co., Ltd., Tokyo (JP)

( * ) Notice: Subject to any disclaimer, the term of this patent is extended or adjusted under 35 U.S.C. 154(b) by 140 days.

(21) Appl. No.: 12/675,207

(22) PCT Filed: Aug. 27, 2008

(86) PCT No.: PCT/JP2008/065297
§ 371 (c)(1),
(2), (4) Date: Jul. 12, 2010

(87) PCT Pub. No.: WO2009/028551
PCT Pub. Date: Mar. 5, 2009

(65) Prior Publication Data
US 2010/0278397 A1  Nov. 4, 2010

(30) Foreign Application Priority Data
Aug. 31, 2007  (JP) .................................. 2007-227124

(51) Int. Cl.
*G06K 9/00* (2006.01)
(52) U.S. Cl. ........................................ 382/124; 382/115
(58) Field of Classification Search .................. 382/115, 382/124, 127; 283/68; 356/71
See application file for complete search history.

(56) References Cited

U.S. PATENT DOCUMENTS

| | | | |
|---|---|---|---|
| 6,526,160 B1 * | 2/2003 | Ito | 382/117 |
| 6,545,715 B1 * | 4/2003 | Na | 348/351 |
| 6,650,779 B2 * | 11/2003 | Vachtesvanos et al. | 382/228 |
| 7,174,032 B2 | 2/2007 | Takiguchi et al. | |
| 7,310,434 B2 * | 12/2007 | Shigeta | 382/125 |
| 7,804,984 B2 * | 9/2010 | Sidlauskas et al. | 382/124 |
| 7,835,547 B2 | 11/2010 | Kawata | |
| 7,889,885 B2 * | 2/2011 | Cordery et al. | 382/101 |
| 2002/0054694 A1 * | 5/2002 | Vachtsevanos et al. | 382/111 |
| 2004/0208395 A1 * | 10/2004 | Nomura | 382/275 |
| 2008/0025580 A1 * | 1/2008 | Sidlauskas et al. | 382/124 |

FOREIGN PATENT DOCUMENTS

| | | |
|---|---|---|
| JP | 2003-150962 A | 5/2003 |
| JP | 2005-346654 A | 12/2005 |

OTHER PUBLICATIONS

Office action issued Jan. 24, 2012 in a counterpart application JP2007-227124.
English abstract of JP2003-150962 A published May 23, 2003.
English abstract of JP2005-346654 A published Dec. 15, 2005.

* cited by examiner

*Primary Examiner* — Brian Q Le
*Assistant Examiner* — Edward Park
(74) *Attorney, Agent, or Firm* — Novak Druce + Quigg LLP

(57) ABSTRACT

In view of the fact that the reproducibility of a finger vein pattern is deteriorated in an image of the finger vein due to external scattered light, displacement, change in the amount of blood flow and the like, a multiple-valued pattern matching method is adopted so that such changes can be dealt with by converting a data map itself into a multiple-valued map.

8 Claims, 6 Drawing Sheets

AUTHENTICATION DEVICE AND AUTHENTICATION METHOD

CROSS REFERENCE TO RELATED APPLICATION

This application is a U.S. national stage application of International Application No. PCT/JP2008/065297, filed Aug. 27, 2008, which designates the U.S. and claims priority to Japanese Pat. App. No. JP2007-227124, filed Aug. 31, 2007, each of which are incorporated herein by reference in their entireties,

TECHNICAL FIELD

The present invention relates to an authentication apparatus for personal identification based on finger vein patterns, and an authentication method thereof.

BACKGROUND ART

Conventionally, personal identification is performed by comparing veins and finger prints with feature point extraction data obtained by the minutia method (for example, Patent Document 1).

The feature point extraction method is generally considered invulnerable to rotation or displacement. In reality, however, when rotation or displacement actually occurs, the feature point extraction method has a problem that the brightness of an image changes so greatly that important feature points are lost in many cases.

In addition, the brightness of the image also changes greatly due to scattered light or indirect reflection light of the sunlight, or due to change in the amount of blood flow depending on an outdoor air temperature. As a result, feature points at a finger joint and an edge portion of the finger are lost, and thereby the authentication score decreases.

Patent Document 1: Japanese Patent Application Publication No. 2001-243465.

DISCLOSURE OF THE INVENTION

Problem to be Solved by the Invention

The problem to be solved by the invention is to achieve highly accurate authentication even if some feature points are lost as a result of rotation or displacement of a finger when the finger is placed on a scanner, or as a result of change in the brightness of the image.

Means for Solving the Problem

In view of the fact that the reproducibility of a finger vein pattern is deteriorated in an image of the finger vein due to external scattered light, displacement, change in the amount of blood flow and the like, a multiple-valued pattern matching method is adopted so that such changes can be dealt with by converting a data map itself into a multiple-valued map.

A first aspect of the present invention includes an authentication apparatus comprising: a light source that emits an infrared light beam onto a finger; image pick-up means that picks up an image of the finger by using a transmitted light beam, and thus outputs an image signal; low-frequency brightness component extracting means that extracts a low-frequency brightness component signal from the image signal by using a low-pass filter; middle-frequency brightness component extracting means that extracts a middle-frequency brightness component signal from the image signal by using a middle-pass filter; correction means that corrects the middle-frequency brightness component signal by using the low-frequency brightness component signal; quaternary-value converting means that converts the corrected middle-frequency brightness component signal into quaternary values such that the quaternary values are distributed at a predetermined ratio; storage means that stores a quaternary-valued image obtained from the quaternary-value conversion by the quaternary-value converting means; correlation coefficient calculating means that calculates a correlation coefficient between a quaternary-valued evaluation image as an object of evaluation and a quaternary-valued registered image by using a pattern matching method based on a normalized correlation method, the quaternary-valued evaluation image obtained from the quaternary-value conversion by the quaternary-value converting means, the quaternary-valued registered image being beforehand stored in the storage means; and judgment means that judges whether or not the quaternary-valued evaluation image and the quaternary-valued registered image are images picked up from the same finger on a basis of the correlation coefficient which is calculated by the correlation coefficient calculating means.

Descriptions will be provided for an example of the process of extracting the low-frequency brightness component signal from the image signal by using the low-pass filter.

For example, by the moving average method, a value representing a particular pixel is set to be equal to an average of values representing the respective neighboring pixels of the particular pixel. For example, let us assume that, before the process, the brightness of each pixel in a 3×3 image region is as shown in Table 1. After the process, a value representing the brightness of a pixel at coordinates (2,2) is set at "2", because $(2+2+2+1+1+1+3+3+3)/9=2$.

TABLE 1

| 2 | 2 | 2 |
|---|---|---|
| 1 | 1 | 1 |
| 3 | 3 | 3 |

The middle-frequency brightness component signal is extracted by using a middle-pass filter (band-pass filter) which removes low frequencies by using a matrix in which weights assigned to the respective pixels decrease by $2/3$ in geometric series as the pixels become farther from the center, and then removes high-frequencies by the moving average method.

For example, let us assume that: as shown in Table 2, a coefficient of a pixel at coordinates (3,3) is set at 12.44; coefficients of pixels at coordinates (2,2), (2,3), (2,4), (3,1), (3,3), (4,2), (4,3) and (4,4) are set at −0.67; and coefficients of pixels at coordinates (1,1), (1,2), (1,3), (1,4), (1,5), (2,1), (2,5), (3,1), (3,5), (4,1), (4,5), (5,1), (5,2), (5,3), (5,4) and (5, 5) are set at −0.44.

Note that: $0.67=2/3$; and $0.44=4/9=(2/3)^2$.

TABLE 2

| −0.44 | −0.44 | −0.44 | −0.44 | −0.44 |
|---|---|---|---|---|
| −0.44 | −0.67 | −0.67 | −0.67 | −0.44 |
| −0.44 | −0.67 | 12.44 | −0.67 | −0.44 |
| −0.44 | −0.67 | −0.67 | −0.67 | −0.44 |
| −0.44 | −0.44 | −0.44 | −0.44 | −0.44 |

"To correct the middle-frequency brightness component signal using the low-frequency brightness component signal"

means, for example, that (middle-frequency brightness component signal)÷(low-frequency brightness component signal).

Descriptions will be provided for "to convert the corrected middle-frequency brightness component signal into a quaternary value so that quaternary values of the middle-frequency brightness component signal are distributed at a predetermined ratio".

"To convert the corrected middle-frequency brightness component signal into a quaternary value" means, for example, that the corrected middle-frequency brightness component signal is converted into a quaternary value "0" when the signal is less than a first threshold, another quaternary value "1" when the signal is not less than the first threshold but less than a second threshold, yet another quaternary value "2" when the signal is not less than the second threshold but less than a third threshold, and still another quaternary value "3" when the signal is not less than the third threshold.

"So that quaternary values of the middle-frequency brightness component signal are distributed at a predetermined ratio" means, for example, that the relationship in quantity between the quaternary value "0" and the whole quaternary values is 80%; the relationship in quantity between the quaternary value "1" and the whole quaternary values is 5%; the relationship in quantity between the quaternary value "2" and the whole quaternary values is 5%; and the relationship in quantity between the quaternary value "3" and the whole quaternary values is 10%. It is desirable that, whenever deemed necessary, the ratio among the quaternary values "0", "1", "2", and "3" should be adjusted depending on the brightness of the light source, the sensitivity of image-pickup means, and the like.

Descriptions will be provided for "calculating a correlation coefficient between a quaternary-valued evaluation image as an object of evaluation, and a quaternary-valued registered image by using the pattern matching method based on a normalized correlation method, the quaternary-valued evaluation image being converted into a quaternary value by the quaternary-value converting means, the quaternary-valued registered image being beforehand stored in the storage means".

The quaternary-valued evaluation image as the object of evaluation means a quaternary-valued image which is intended to be evaluated in terms of whether the quaternary-valued image coincides with any one of multiple quaternary-valued registered images.

The "correlation coefficient" is found by, for example,
(a value of cross-correlation between the registered image and the evaluation image)÷(a value of autocorrelation of the registered image). The value of cross-correlation and the value of autocorrelation will be explained later.

The "pattern matching method based on a normalized correlation method" is a method in which:

(1) the correlation coefficient between the registered image and the evaluation image is calculated;

(2) the relative locations of the two images are shifted, and a correlation coefficient between the two resultant images is calculated; and (3) multiple correlation coefficients between the two images are calculated by repeating the calculation process numbered (2), and a correlation coefficient whose value is the largest among those of the respective thus-calculated correlation coefficients is selected as a definitive correlation coefficient.

"To judge whether or not the quaternary-valued evaluation image and the quaternary-valued registered image are obtained by picking up the respective images of the same finger on a basis of the correlation coefficient calculated by the correlation coefficient calculating means" means, for example, that: when the correlation coefficient is equal to or more than a predetermined value, the images are judged as being obtained by photographing the same finger; and when the correlation coefficient is less than the predetermined value, the images are judged as being obtained by photographing the respective different fingers.

A second aspect of the present invention is one in which the correlation coefficient calculating means calculates the correlation coefficient by using the following formula 2, $$\text{correlation coefficients} = F/G \qquad \text{[Formula 2]}$$

where: F represents a value of cross-correlation between the evaluation image and the registered image, and is defined as $F=\Sigma(I \times T)$; G represents a value of autocorrelation of the registered image, and is defined as $G=\Sigma(T \times T)$; I denotes a brightness of the evaluation image; and T denotes a brightness of the registered image.

A third aspect of the present invention is one which further comprises quaternary-valued reduced image generating means that generates a quaternary-valued reduced image by convolving a plurality of cells included in the quaternary-valued image obtained from the quaternary-value conversion by the quaternary-value converting means, wherein: the correlation coefficient calculating means calculates a primary correlation coefficient between a quaternary-valued reduced evaluation image generated from the quaternary-valued evaluation image, and a quaternary-valued reduced registered image beforehand stored in the storage means, by using the pattern matching method based on the normalized correlation method; and only when the primary correlation coefficient is not less than a predetermined value, the correlation coefficient calculating means calculates the correlation coefficient between the quaternary-valued evaluation image associated with the quaternary-valued reduced evaluation image, and the quaternary-valued registered image associated with the quaternary-valued reduced registered image, by using the pattern matching method based on the normalized correlation method.

The convolution will be described later.

A fourth aspect of the present invention is to one which further comprises a high-frequency brightness component extracting means that extracts a high-frequency brightness component signal from the image signal by using a high-pass filter, wherein: the correction means corrects the middle-frequency brightness component signal and the high-frequency brightness component signal by using the low-frequency brightness component signal; the quaternary-value converting means converts the corrected middle-frequency brightness component signal into quaternary values such that the quaternary values are distributed at a first predetermined ratio, and converts the corrected high-frequency brightness component signal into quaternary values such that the quaternary values are distributed at a second predetermined ratio; the correlation coefficient calculating means calculates (1) a middle-frequency correlation coefficient between a quaternary-valued middle-frequency evaluation image obtained from the middle-frequency brightness component signal, and a quaternary-valued middle-frequency registered image beforehand stored, and (2) a high-frequency correlation coefficient between a quaternary-valued high-frequency evaluation image obtained from the high-frequency brightness component signal, and a quaternary-valued high-frequency registered image beforehand stored; and on the basis of the middle-frequency correlation coefficient and the high-frequency correlation coefficient, the judgment means judges whether or not the quaternary-valued middle-frequency evaluation image and the quaternary-valued middle-frequency registered image are images picked up from the same finger, and whether or not the quaternary-valued high-frequency evaluation image and the quaternary-valued high-frequency registered image are images picked up from the same finger.

The high-pass filter will be described later.

"To correct the middle-frequency brightness component signal and the high-frequency brightness component signal using the low-frequency brightness component signal" means, for example, that (the middle-frequency brightness component signal)÷(the low-frequency brightness component signal), and (the high-frequency brightness component signal)÷(the low-frequency brightness component signal).

It does not matter whether the distribution (first predetermined ratio) of quaternary values of the middle-frequency brightness component signal and the distribution (second predetermined ratio) of quaternary values of the high-frequency brightness component signal are equal to or different from each other.

"To judge whether or not the quaternary-valued middle-frequency evaluation image and the quaternary-valued middle-frequency registered image are obtained by picking up the respective images of the same finger on a basis of the middle-frequency correlation coefficient, and to judge whether or not the quaternary-valued high-frequency evaluation image and the quaternary-valued high-frequency registered image are obtained by picking up the respective images of the same finger on a basis of the high-frequency correlation coefficient" means, for example, that:

(1) when the high-frequency correlation coefficient (the correlation coefficient concerning an inter-joint dermal print image) is less than 0.3, the authenticity is determined as NG (i.e., it is judged that the quaternary-valued evaluation image and the quaternary-valued registered image are not obtained by picking up the respective images of the same finger);

(2) when the middle-frequency correlation coefficient (the correlation coefficient concerning a vein image) is not less than 0.5, the authenticity is determined as OK (i.e., it is judged that the quaternary-valued evaluation image and the quaternary-valued registered image are obtained by picking up the respective images of the same finger);

(3) when the middle-frequency correlation coefficient is less than 0.3, the authenticity is determined as NG; and (4) when the middle-frequency correlation coefficient is not less than 0.3 but less than 0.5, the authenticity is determined as OK if B≧0.5, where B={(the correlation coefficient concerning the vein image−0.3}×2+(the correlation coefficient concerning the inter-joint dermal print image)×0.6).

Effects of the Invention

According to a first aspect of the present invention, authentication with high environmental resistance can be achieved, with high reproducibility, by converting each bit into a value represented by a multiple-valued number. In addition, authentication dealing with change in the amount of blood flow can also be achieved.

According to a third aspect of the present invention, both the quaternary-valued image and the quaternary-valued reduced image are produced so that authentication is carried out by two steps. This makes it possible to perform evaluation with a large number of object images at high speed.

According to a fourth aspect of the present invention, both a vein and an inter-joint dermal print of a finger are simultaneously evaluated by transmitted light from the same light source. Thus, an authentication method can be achieved in which an image of a finger is difficult to forge. In addition, evaluation can be performed more accurately than in the case where only the vein is used.

| EXPLANATION OF REFERENCE NUMERALS | |
|---|---|
| 1 | infrared LED |
| 2 | first user interface |
| 3 | second user interface |
| 4 | touch sensor |
| 5 | infrared LED driving circuit |
| 6 | CPU |
| 7 | memory |
| 8 | camera |
| 9 | video decoder |
| 10 | FPGA |

BEST MODES FOR CARRYING OUT THE INVENTION

Referring to FIGS. 1 to 5, descriptions will be hereinbelow provided for a finger vein authentication apparatus according to a first embodiment of the present invention.

Figure 1:
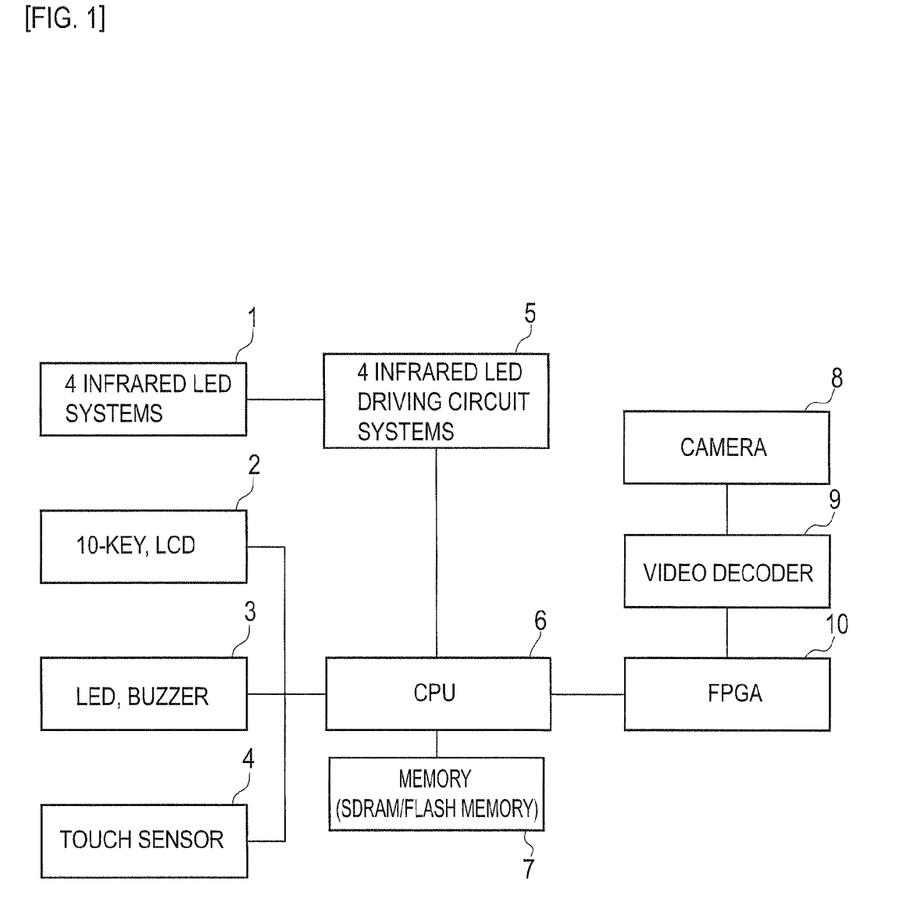
FIG. 1 is a diagram showing an overall configuration of an authentication apparatus according to an embodiment of the present invention.

FIG. 1 shows an overall configuration of the finger vein authentication apparatus according to the first embodiment. As shown in FIG. 1, the finger vein authentication apparatus includes: a light source 1 including 4 infrared LED (light-emitting diode) systems; a first user interface 2 including a 10-key and a LCD (liquid crystal display); a second user interface 3 including an LED and a buzzer; a finger detector 4 including a touch sensor; an infrared LED driving circuit capable of controlling electric currents of the respective 4 systems; a CPU (central processing unit) 6 that controls operations of various parts; a memory 7 used as a work memory for the CPU, and also used to retain data on veins; a camera 8 that picks up an image of veins; a video decoder 9 that converts an camera image into a set of digital data; and an FPGA (field programmable gate array) 10 that converts the set of digital video data into a set of data on brightness. The memory 7 includes SDRAM (synchronous dynamic random access memory), a flash memory and the like.

Figure 2:
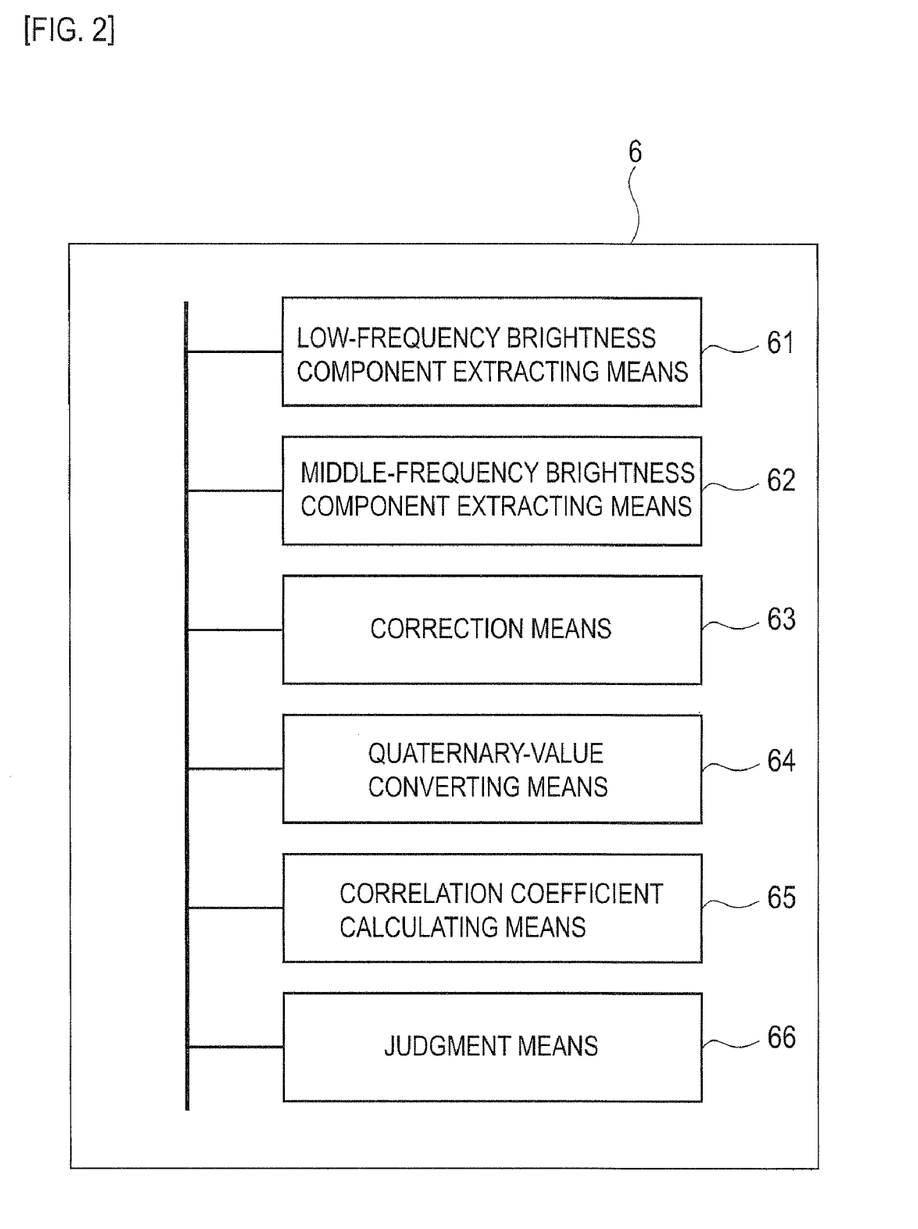
FIG. 2 is a diagram showing a configuration of an authentication executing unit according to the embodiment of the present invention.

FIG. 2 shows a configuration of an authentication executing unit according to the first embodiment. The CPU 6 functions as the authentication executing unit under control of software.

Specifically, the CPU 6 function as: low-frequency brightness component extracting means 61 that extracts a low-frequency brightness component signal from an image signal using a low-pass filter; middle-frequency brightness component extracting means 62 that extracts a middle-frequency brightness component signal from the image signal using a middle-pass filter; correction means that corrects the middle-frequency brightness component signal using the low-frequency brightness component signal; quaternary-value converting means 64 that converts the corrected middle-frequency brightness component signal into a quaternary value so that quaternary values are distributed at a predetermined ratio; correlation coefficient calculating means 65 that calculates a correlation coefficient between a quaternary-valued evaluation image as an object of evaluation, the quaternary-valued evaluation image being converted into a quaternary value by the quaternary-value converting means, and a quaternary-valued registered image, the quaternary-valued registered image being beforehand stored in the storage means, by using a pattern matching method based on a normalized correlation method; and judgment means 66 that judges whether or not the quaternary-valued evaluation image and the quaternary-valued registered image are obtained by picking up the respective images of the same finger on a basis of the correlation coefficient which is calculated by the correlation coefficient calculating means 65.

Figure 3:
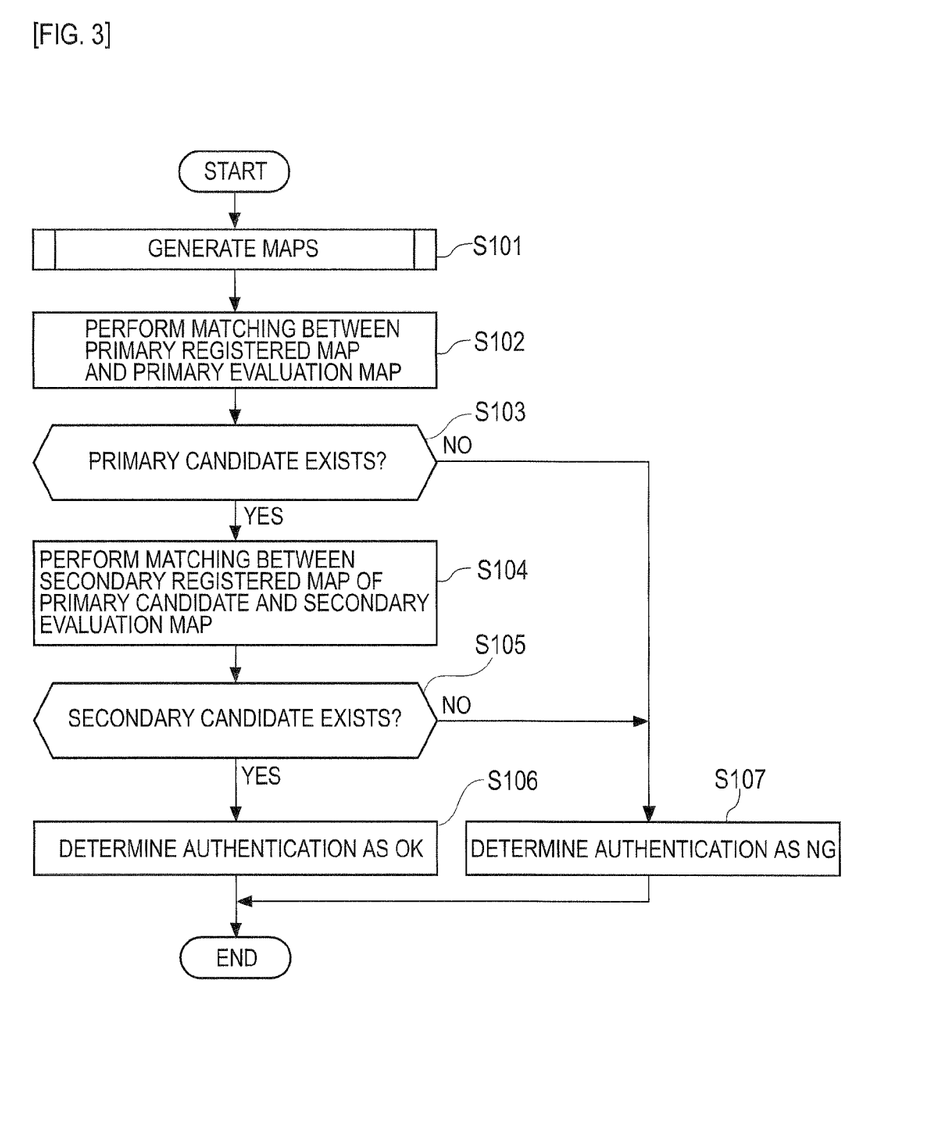
FIG. 3 is a diagram showing an overall flow of an authentication process according to the embodiment of the present invention.

FIG. 3 shows an overall flow of an authentication process according to the first embodiment. As shown in FIG. 3, maps (quaternary-valued images) are generated in step S101. Specifically, a primary registered map, a secondary registered map, a primary evaluation map and a secondary evaluation map are generated. The primary registered map and the secondary registered map are beforehand generated and stored in the memory 7.

In step S102, a screening (primary authentication) is carried out using primary maps (thumbnail dictionaries) Specifically, a matching is performed between each of primary maps stored in the memory 7 and a primary map as an object of evaluation generated from an image of veins captured by the camera 8. Primary maps, whose matching result evaluation values (similarity evaluation values) are higher than a limit value, are selected as primary candidates.

In a case where the number of primary maps, whose matching result evaluation values (similarity evaluation values) are higher than the limit value, is larger than a predetermined number, it is desirable that primary maps, whose ranks are higher than a predetermined rank, should be selected as the primary candidates. For example, in a case where the number of primary maps, whose matching result evaluation values are higher than the limit value, is equal to or more than 10, it is desirable that primary maps, whose matching result evaluation values are the first to 10th largest, should be selected as the primary candidates.

If any primary candidate exists (or if YES in step S103), the process proceeds to step S104. If no primary candidate exits (or if NO in step S103), the process proceeds to step S107.

In step S104, a secondary authentication process is carried out using secondary maps. Specifically, a matching is performed between each of the stored secondary maps which are associated with the respective primary candidates selected by the primary screening (primary authentication), and a secondary map of the object of evaluation, which is generated from the image of the veins captured by the camera 8. Secondary maps, whose matching result evaluation values (similarity evaluation values) is higher than a limit value, are selected as secondary candidates.

If any secondary candidate exists (or if YES in step S105), the process proceeds to step S106. If no secondary candidate exits (or if NO in step S105), the process proceeds to step S107.

In step S106, in a case where a score (description of the score will be given later) of a secondary map having the highest matching result evaluation values (similarity evaluation values) is higher than a threshold value, authentication is determined as OK. In step S107, authentication is determined as NG.

Figure 4:
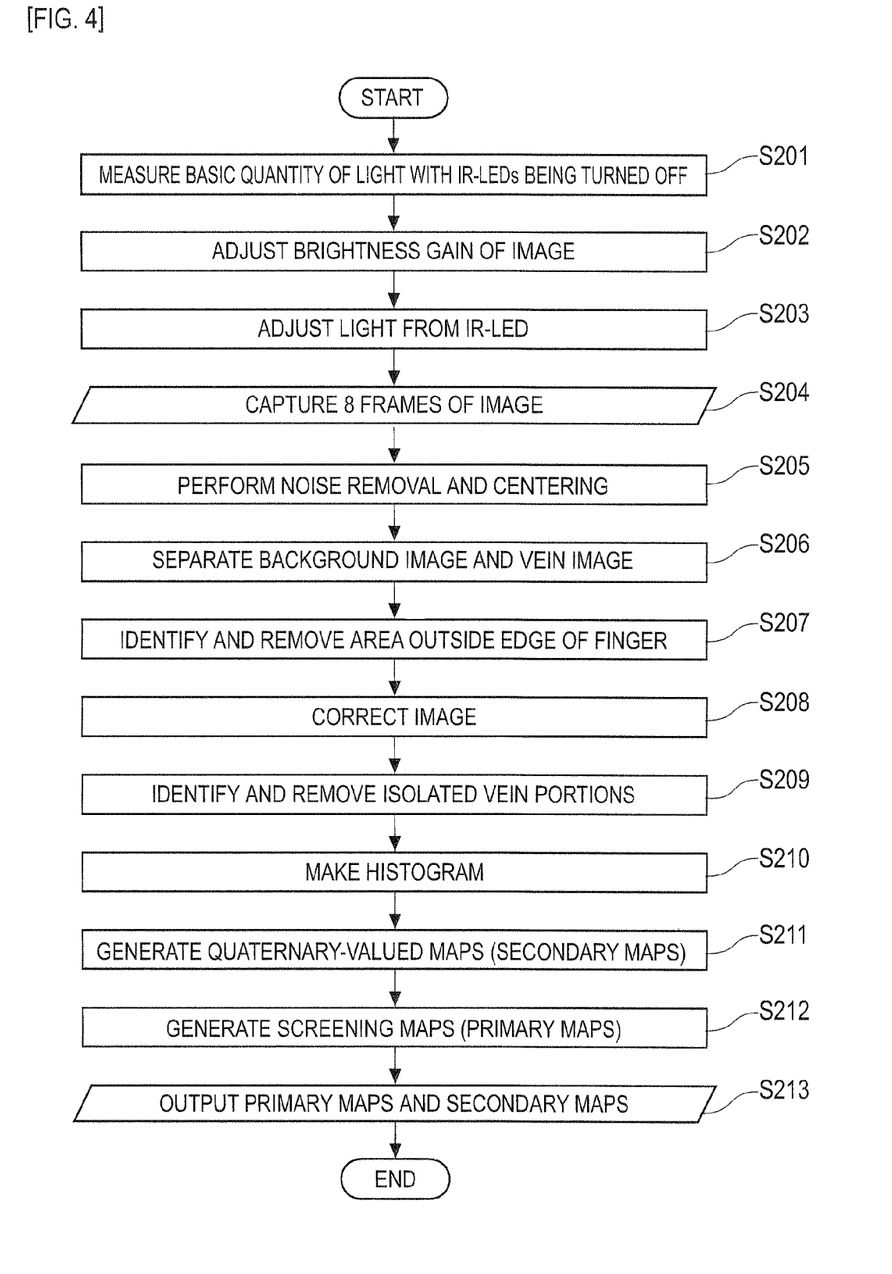
FIG. 4 is a diagram showing a flow of a map generating process according to the embodiment of the present invention.

FIG. 4 shows a flow of a map generating process according to the first embodiment. As shown in FIG. 4, a basic quantity of light is measured with the IR-LEDs (infrared light-emitting diodes) being turned off in step S201, and a brightness gain of an image is adjusted in step S202.

In step S203, light from an IR-LED is adjusted. Specifically, an optimal quantity of light is emitted onto an object of evaluation from the IR-LED, and the brightness gain of the image is finely tuned.

In step S204, 8 frames of image are captured. Thus, for each pixel in the same coordinates throughout all the frames, a simple sum of brightness is calculated.

In step S205, a camera noise is removed, and a centering process is carried out. The centering process means a process of making the center of the image and the center of each frame coincide with each other.

In step S206, separation is performed on a background image and a vein image. Specifically, the background image (represented by a low-frequency brightness component signal) is separated from the 8 frames using a low-pass filter, and the vein image (represented by a middle-frequency brightness component signal) is separated from the same 8 frames using a band-pass filter.

The separation of the low-frequency brightness component signal from the 8 frames is achieved using the moving average method. Specifically, the separation of the low-frequency brightness component is achieved by setting the brightness of the center pixel (namely, a pixel at coordinates (11, 11) at an arithmetic mean of brightnesses of the respective 21×21 pixels.

The separation of the middle-frequency brightness component signal from the 8 frames is achieved as follows. To begin with, the low-frequency brightness component signal is separated using a filter which decreases the weights assigned to the respective 21×21 pixels by ⅔ in geometric series as the pixels become farther from the center. Subsequently, for each 3×3 pixels, the brightness of a pixel at the center (or at coordinates (2, 2)) is set at an arithmetic mean of the brightnesses of the 3×3 pixels.

In step S207, an area outside the edge of the finger is located and removed from each frame. In step S208, the vein image is corrected using the background image. Specifically, the middle-frequency brightness component signal is divided by the low-frequency brightness component signal.

In step S209, isolated vein portions whose reproducibility is low are located and removed. The "isolated vein portions" mean portions of a vein which are photographed as isolated pieces but not reproduced as a single vein. The removal of the isolated vein portions enhances the reproducibility for recognition.

[Example of Removal of an Isolated Vein Portion]

(1) When a brightness f(x, y) of coordinates (x, y) is more than 1, a length of line segment is set at 1. In this respect, the brightness is represented by a quaternary value.

(2) Thereafter, coordinates whose brightness is more than 1 are searched for in the vicinity of the coordinates.

(3) Each time coordinates whose brightness is more than 1 are found in the vicinity thereof, 1 is added to the length of line segment, and the search is continued.

(4) If no coordinates whose brightness is more than 1 exist in the vicinity thereof, the search is terminated.

(5) If a total length of line segment at a time when the search is terminated is less than 10, the line segment is regarded as an isolated vein portion, and the entire line segment is set at 0.

Through the processes numbered (1) to (5), isolated vein portions whose reproducibility is low can be removed.

In this respect, the "vicinity" includes coordinates (x, y+1), (x, y−1), (x+1, y), (x+1, y+1) and (x+1, y−1) surrounding coordinates (x, y).

In step S210, a histogram is made. In step S211, secondary maps (quaternary-valued maps) are generated. In the present embodiment, in each frame, the brightness of each pixel is represented by a value in a range of 0 to 255. Then, the brightnesses of each pixel in the 8 frames are summed up. In other words, the total brightness of each pixel takes a value in a range of 0 to 2040. Thereafter, the value in the range of 0 to 2040 is converted into quaternary values so that the ratio among 0s, 1s, 2s and 3s can be a predetermined value.

For example, let us assume that: the quaternary value takes "0" when the total brightness is less than a first threshold; the quaternary value takes "1" when the total brightness is not less than the first threshold but less than a second threshold; the quaternary value takes "2" when the total brightness is not less than the second threshold but less than a third threshold; and the quaternary value takes "3" when the total brightness is not less than the third threshold. In this case, the first threshold, the second threshold and the third threshold are determined so that: the ratio of "0" can be 80%; the ratio of "1" can be 5%; and the ratio of "2" can be 5%.

A clear image is not always acquired from a vein. In a case where a vein image is not clear, if the image is represented by binary values and thus processed as if a clear image were instead acquired, it is difficult to reflect the unclearness of the image on the evaluation. In contrast, when the image is represented by quaternary values, it is possible to reflect the unclearness of the image on the evaluation.

In step S212, the primary maps (thumbnail dictionaries) are generated. The generation of the primary maps is carried out in order to make the operation faster, and to make the operation meet the cache capacity of the CPU. In step S213, the primary maps and the secondary maps are outputted.

For each person who is a subject of authentication evaluation, primary maps and secondary maps are generated. It is desirable that multiple primary maps should be generated for each finger of each person who is a subject of authentication evaluation. Similarly, it is desirable that multiple secondary maps should be generated for each finger of each person who is a subject of authentication evaluation. For example, let us assume a case where persons who are subjects of authentication evaluation are Messrs. A, B and C, i.e., a case where an authentication process is performed so as to evaluate who among Messrs. A, B and C places a finger on the authentication apparatus. For a middle finger of Mr. A, three primary maps and three secondary maps are generated. Similarly, three primary maps and three secondary maps are generated for a middle finger of each of Messrs. B and C. In this respect, it does not matter whether or not the number of generated primary maps is equal to the number of generated secondary maps. All the primary and secondary maps thus generated are stored in the memory 7.

Further descriptions will be provided for how the second maps are generated. For example, let us assume that, when the 8 frames are combined together, the total brightness of each pixel comes as shown in Table 3.

TABLE 3

| 0 | 1824 | 0 |
|---|------|---|
| 256 | 511 | 1122 |
| 660 | 906 | 1624 |

The total brightness of each pixel is converted into a quaternary value so that the ratios of the numbers of 0s, 1s, 2s and 3s to the number of quaternary values are all 25%. In this respect, for the purpose of simplifying the explanation, it is assumed that the ratios of the numbers of 0s, 1s, 2s and 3s to the number of quaternary values are equal to one another. However, the ratios of the numbers of 0s, 1s, 2s and 3s to the number of quaternary values may be arbitrarily determined. It does not matter if the ratios of the numbers of 0s, 1s, 2s and 3s to the number of quaternary values are not equal to one another.

In the following case, the quaternary value takes "0" when the total brightness of a pixel in the 8 combined frame is less than 400; the quaternary value takes "1" when the total brightness thereof is not less than 400 but less than 800; the quaternary value takes "2" when the total brightness thereof is not less than 800 but less than 1200; and the quaternary value takes "3" when the total brightness thereof is not less than 1200. In this manner, the total brightness of each pixel is converted into a quaternary value as shown in Table 4.

TABLE 4

| 0 | 3 | 0 |
|---|---|---|
| 0 | 1 | 2 |
| 1 | 2 | 3 |

Next, descriptions will be provided for how the primary maps (thumbnail dictionaries) are generated (convolved).

Descriptions will be provided for a relationship between the secondary maps (dictionaries for authentication) and the primary maps (thumbnail dictionaries) on the basis of Tables 5 and 6. For example, let us assume that a 2×2 primary map is generated from a 4×4 secondary map by convolving each 2×2 into one. A brightness at (1, 1) in the primary map is calculated on the basis of brightnesses at (1, 1), (1, 2), (2, 1) and (2, 2) in the secondary map. Similarly, a brightness at (1, 2) in the primary map is calculated on the basis of brightnesses at (1, 3), (1, 4), (2, 3) and (2, 4) in the secondary map; a brightness at (2, 1) in the primary map is calculated on the basis of brightnesses at (3, 1), (3, 2), (4, 1) and (4, 2) in the secondary map; and a brightness at (2, 2) in the primary map is calculated on the basis of brightnesses at (3, 3), (3, 4), (4, 3) and (4, 4) in the secondary map. In this respect, coordinates (X, Y) means the X-th row and the Y-th column in a matrix.

TABLE 5

| Secondary Map of 4 × 4 | | | |
|---|---|---|---|
| (1, 1) | (1, 2) | (1, 3) | (1, 4) |
| (2, 1) | (2, 2) | (2, 3) | (2, 4) |
| (3, 1) | (3, 2) | (3, 3) | (3, 4) |
| (4, 1) | (4, 2) | (4, 3) | (4, 4) |

TABLE 6

| Primary Map of 2 × 2 | |
|---|---|
| (1, 1) | (1, 2) |
| (2, 1) | (2, 2) |

The brightness values in the primary map are calculated from the brightness values in the secondary map in the following manner.

(1) The medians of thresholds for the respective pixels in the secondary map are summed up.

(2) The value obtained by the summing-up is divided by the number of pixels which are targets of the convolution.

(3) The value obtained by the division is converted into a quaternary value, and the thus-obtained quaternary value is assigned to the cell in the primary map.

(4) At this time, the ratio among the numbers of 0s, 1s, 2s and 3s are set at a predetermined ratio as is the case with the generation of the secondary map.

Note that, it is assumed that the median of the threshold= (upper threshold+lower threshold)/2.

For example, the median of the thresholds (the lower threshold is 0, whereas the upper threshold is 400) for a value "0" in the secondary map is "200"; the median of the thresholds (the lower threshold is 400, whereas the upper threshold is 800) for a value "1" in the secondary map is "600"; and the median of the thresholds (the lower threshold is 800, whereas the upper threshold is 1200) for a value "2" in the secondary map is "1000".

In addition, for the purpose of simplifying the explanation, the median of the threshold (in a range of 1200 to 2047) for a value "3" in the secondary map is set at "1600".

Detailed descriptions will be provided using FIG. 7.

TABLE 7

| 0 | 0 | 0 | 1 |
|---|---|---|---|
| 0 | 1 | 1 | 2 |

For example, at (1, 1), (1, 2), (2, 1) and (2, 2) in the secondary map:

A value at (1, 1) is "0", and the median corresponding to "0" is "200";

A value at (1, 2) is "0", and the median corresponding to "0" is "200";

A value at (2, 1) is "0", and the median corresponding to "0" is "200"; and

A value at (2, 2) is "1", and the median corresponding to "1" is "600".

For this reason, the sum of the medians is (200+200+200+ 600)=1200, and a value "300" is calculated by dividing the sum by the number of pixels "4".

In addition, at (1, 3), (1, 4), (2, 3) and (2, 4):

A value at (1, 3) is "0", and the median corresponding to "0" is "200";

A value at (1, 4) is "1", and the median corresponding to "1" is "600";

A value at (2, 3) is "1", and the median corresponding to "1" is "600"; and

A value at (2, 4) is "2", and the median corresponding to "2" is "1000".

For this reason, the sum of the medians is (200+600+600+ 1000)=2400, and a value "600" is calculated by dividing the sum by the number of pixels "4".

Similarly, values representing all the cells constituting the primary map are found. Subsequently, all the thus-found values are converted into quaternary values so that the ratio in numbers among the quaternary values can be a predetermined ratio. In this manner, the primary map is generated from the secondary map.

Figure 5:
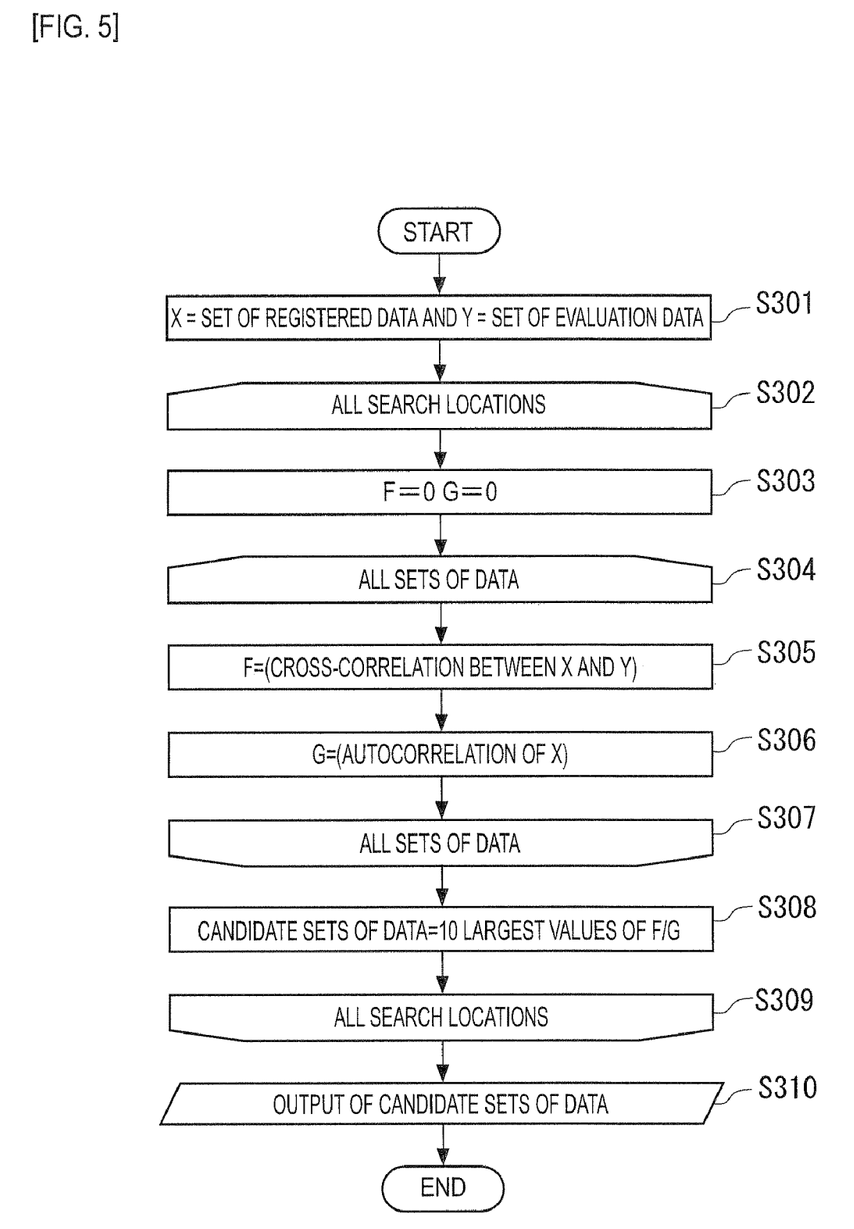
FIG. 5 is a diagram showing a flow of a matching process according to the embodiment of the present invention.

FIG. 5 shows a flow of a matching process according to the first embodiment. As shown in FIG. 5, in step S301, X and Y are defined as X=a set of registered data and Y=a set of evaluation data. In step S302, a loop of the matching process starts to be applied to all the search locations. In step S303, as an initial value, 0 is substituted for X and Y. In step S304, a loop of the matching process starts to be applied to all the sets of data. In this respect, (1) the term "all the sets of data" means all the registered primary maps (thumbnail dictionaries) when the matching process is executed using the primary maps, and (2) the term "all the sets of data" means all the secondary maps associated with each primary candidate when the matching process is executed using the secondary maps.

In step S305, a cross-correlation between X and Y is calculated, and the thus-calculated value is substituted for F. In step S306, an autocorrelation of X is calculated, and the thus-calculated value is substituted for G. In step S307, the loop of the matching process to all the sets of data is terminated. In step S308, F/G is calculated for each set of data. Among the values obtained by the calculation, the 10 largest values are selected as candidate sets of data. In step s309, the loop of the matching process to all the search locations is terminated. In step S310, the candidate sets of data are outputted. Detailed contents of each step will be described later.

When image search (matching) is performed, if the number of registered maps (the number of sets of map data stored in the memory 7) is large, most of the time used for the search is consumed to check whether or not the evaluation image and each registered image match together in position. For this reason, whether or not the evaluation image and each registered image match together in position is checked in one stage, and how much the evaluation image and each registered image coincide together is evaluated in the other stage (i.e., the primary evaluation and the secondary evaluation are executed separately).

In the first stage (primary evaluation), whether or not the evaluation image and each registered image match together in position, and whether or not the evaluation image and each registered image are similar to each other, are roughly evaluated using rough images (primary maps) When the rough images (primary maps) are used, the process speed can be made faster by two to three digits. In the second stage (secondary evaluation), the evaluation image and each registered image are fitted to each other in a fine tune, and how much the evaluation image and each registered image coincide together is evaluated with high accuracy.

The time needed for the process can be reduced without sacrificing the quality of the evaluation, when whether or not the evaluation image and each registered image match together in position is checked in one stage, and how much the evaluation image and each registered image coincide together is evaluated in the other stage.

Descriptions will be provided for how the correlation coefficient between each set of registered data and the set of evaluation data is calculated. Table 8 shows an example of a set of registered data.

TABLE 8

| 0 | 0 | 1 | 0 |
|---|---|---|---|
| 0 | 1 | 2 | 1 |

TABLE 8-continued

| 1 | 2 | 3 | 2 |
|---|---|---|---|
| 2 | 3 | 3 | 3 |

Table 9 shows an example of how a value of autocorrelation $G=\Sigma(T\times T)$ of a set of registered data (registered image) is calculated. In this respect, T denotes a quaternary value into which a brightness of the registered image is converted.

TABLE 9

| | | | | |
|---|---|---|---|---|
| 0 × 0 = 0 | 0 × 0 = 0 | 1 × 1 = 1 | 0 × 0 = 0 | 0 + 0 + 1 + 0 = 1 |
| 0 × 0 = 0 | 1 × 1 = 1 | 2 × 2 = 4 | 1 × 1 = 1 | 0 + 1 + 4 + 1 = 6 |
| 1 × 1 = 1 | 2 × 2 = 4 | 3 × 3 = 9 | 2 × 2 = 4 | 1 + 4 + 9 + 4 = 18 |
| 2 × 2 = 4 | 3 × 3 = 9 | 3 × 3 = 9 | 3 × 3 = 9 | 4 + 9 + 9 + 9 = 31 |
| | | | | 1 + 6 + 18 + 31 = 56 |

Table 10 shows an example of a set of evaluation image.

TABLE 10

| | | | |
|---|---|---|---|
| 0 | 0 | 1 | 2 |
| 0 | 1 | 2 | 3 |
| 0 | 1 | 2 | 3 |
| 1 | 2 | 3 | 3 |

Table 11 shows an example of how a value of cross-correlation $F=\Sigma(I\times T)$ between a registered pattern (set of registered image data) and an evaluation pattern (set of evaluation image data) is calculated. In this respect, I denotes a quaternary value into which a brightness of the evaluation image is converted.

TABLE 11

| | | | | |
|---|---|---|---|---|
| 0 × 0 = 0 | 0 × 0 = 0 | 1 × 1 = 1 | 0 × 2 = 0 | 0 + 0 + 1 + 0 = 1 |
| 0 × 0 = 0 | 1 × 1 = 1 | 2 × 2 = 4 | 1 × 3 = 3 | 0 + 1 + 4 + 3 = 8 |
| 1 × 0 = 0 | 2 × 1 = 2 | 3 × 2 = 6 | 2 × 3 = 6 | 0 + 2 + 6 + 6 = 14 |
| 2 × 1 = 2 | 3 × 2 = 6 | 3 × 3 = 9 | 3 × 3 = 9 | 2 + 6 + 9 + 9 = 26 |
| | | | | 1 + 8 + 14 + 26 = 49 |

In a case where, as shown above, the value of autocorrelation G of the set of registered data is equal to 56 and the value of cross-correlation F between the set of registered data and the set of evaluation data is 49, the correlation coefficient between the set of registered data and the set of evaluation data is equal to 0.875 which results from the division of 49 by 56.

Similarly, a correlation coefficient F/G between the set of evaluation data and all sets of registered data is calculated. After the correlation coefficients for all the sets of registered data are calculated, the set of evaluation data (evaluation map) and the set of registered data (registered map) are relatively shifted vertically or horizontally by one cell, and then the correlation coefficients for all the sets of registered data are again calculated.

The foregoing process is repeated, and the 10 largest correlation coefficients F/G are thus outputted as candidate sets of data (step S310).

The candidate sets of data, which are outputted in step S310, are a result of the matching process shown as step S102 in FIG. 3. In a case where there is a correlation coefficient which is not less than a predetermined among these candidate sets of data, a registered primary map corresponding to the correlation coefficient is selected as a primary candidate in step S103 shown in FIG. 3.

Subsequently, a matching is performed between a secondary registered map associated with the primary candidate and the secondary evaluation map (step S104 shown in FIG. 3). The contents of the matching process are the same as those shown in FIG. 5.

Note that the matching is performed with respect to only the secondary registered map associated with the primary registered map which is judged as the primary candidate in step S103, but not with respect to all the secondary registered maps which are stored in the memory 7.

A matching is performed using the secondary evaluation map and the secondary registered map. Thus, the 10 largest correlation coefficients F/G are outputted as a set of evaluation data (step S310 shown in FIG. 5). The set of evaluation data on correlation, which is outputted in step S310, is a result of the matching in step S104 shown in FIG. 3. In a case where there is a correlation coefficient which is not less than a predetermined value among this set of evaluation data, a secondary registered map corresponding to the correlation coefficient is selected as a secondary candidate in step S105 shown in FIG. 3.

Thus, the original image represented by the set of evaluation data is authenticated as an image of the vein of a person whose data is registered, the image corresponding to the registered secondary map selected as the secondary candidate whose correlation coefficient is the largest among those of the secondary candidates (step S106).

Second Embodiment

A set of data on the inter-joint dermal print and a set of data on the vein are separated from the data of the picked-up image. Thus, an authentication is executed on the basis of the inter-joint dermal print, while another authentication is executed on the basis of the vein. Because the set of data on the inter-joint dermal print and the set of data on the vein are acquired from the single set of data on the pick-up image, an authentication apparatus can be achieved in which data is extremely difficult to forge, while the authentication apparatus requires no specific reflection light source or the like.

In a convention practice, an authentication on a finger print is performed on the basis of an image which is captured from the finger print independently, whereas an authentication on a vein is performed on the basis of an image which is captured from the vein independently.

By contrast, a second embodiment makes it possible to simultaneously perform an authentication on the basis of an inter-joint dermal print (which is a dermal print between the first and second joints from the fingertip on a finger) and an authentication on the basis of a vein with a set of data on the inter-joint dermal print, a set of data on the vein and a set of data on the background being separated from a set of data on an image which is captured from the finger by a single photographic shot.

Specifically, (1) If most of an image represents a pattern of the inter-joint dermal print, the pattern of the inter-joint dermal print is extracted from the image, and an authentication process is performed on the basis of the thus-extracted pattern of the inter-joint dermal print.

(2) If most of an image represents a pattern of the vein, the pattern of the vein is extracted from the image, and an authentication process is performed on the basis of the thus-extracted pattern of the vein.

(3) The image of the background is used for normalizing the gray scales of each of the acquired images.

When the multiple authentication processes are performed in this manner, it is possible to enhance the accuracy of the biometric authentication and the performance of rejecting false fingers and the like.

[Separation of a Background Image]

As in the case of the first embodiment, 8 frames of image are captured, followed by noise removal and centering processes. Then, a background image (represented by a low-frequency brightness component signal) is separated using a low-pass filter.

[Separation of a Vein Image]

As in the case of the first embodiment, 8 frames of image are captured, followed by noise removal and centering processes. Then, a vein image (represented by a middle-frequency brightness component signal) is separated using a band-pass filter.

[Separation of an Inter-Joint Dermal Print Image]

As in the case of the first embodiment, 8 frames of image are captured, followed by noise removal and centering processes. Then, an inter-joint dermal print image (represented by a high-frequency brightness component signal) is separated from the resultant 8 frames using a high-pass filter. The high-pass filter in use is a 21×21, ½ geometric series filter. FIG. 12 shows a 5×5, ½ geometric series filter.

TABLE 12

| | | | | |
|---|---|---|---|---|
| −0.25 | −0.25 | −0.25 | −0.25 | −0.25 |
| −0.25 | −0.5 | −0.5 | −0.5 | −0.25 |
| −0.25 | −0.5 | 8 | −0.5 | −0.25 |
| −0.25 | −0.5 | −0.5 | −0.5 | −0.25 |
| −0.25 | −0.25 | −0.25 | −0.25 | −0.25 |

Once the 8 frames of image is separated into the background image, the vein image and the inter-joint dermal print image, the vein image and the inter-joint dermal print image are corrected using the background image. Afterward, as in the case of the first embodiment, the resultant vein image and the resultant inter-joint dermal print image are converted into quaternary values; for each of the vein image and the inter-joint dermal print image, secondary maps and primary maps (thumbnail images for screening) are generated; and for each of the vein image and the inter-joint dermal print image, match checks are performed using correlation coefficients. Thus, a highly accurate authentication can be performed in which a finger image is difficult to forge.

For example,

1) If a correlation coefficient concerning the inter-joint dermal print image (correlation coefficient concerning the high-frequency) is less than 0.3, the authenticity is rejected (i.e., it is judged that the quaternary-valued evaluation image and the quaternary-valued registered image are not obtained from the same finger).

2) In a case where the correlation coefficient concerning the inter-joint dermal print image is not less than 0.3, (2-1) if a correlation coefficient concerning the vein image (correlation coefficient concerning the middle-frequency) is not less than 0.5, the authenticity is established (i.e., it is judged that the quaternary-valued evaluation image and the quaternary-valued registered image are obtained from the same finger);

(2-2) if the correlation coefficient concerning the vein image than 0.3, the authentic is determined as NG; and (2-3) if the correlation coefficient concerning the vein image is not less than 0.3 but less than 0.5, the authentic is determined as OK when B is not less than 0.5, where B is given by $B = \{(\text{the correlation coefficient concerning the vein image}) - 0.3\} \times 2 + (\text{the correlation coefficient concerning the inter-joint dermal print}) \times 0.6$.

In any of the first and second embodiments, it is desirable that the brightness should be adjusted in the following manner.

[Forgery Prevention Based on Non-Luminous Image]

The finger is discriminated from anything else on the basis of how much an image obtained with no light being emitted from each near infrared LED is changed into an image obtained with light being emitted from the near infrared LED due to only the transmission of the light emitted from the near infrared LED by evaluating the difference between the two images.

[Resistance to External Light Based on Non-Luminous Image]

An amount of light emitted from each near infrared LED and a camera gain, which are used to obtain a target brightness, are controlled by: obtaining an image with no light being emitted from the near infrared LED; and measuring how much bright the thus-obtained image is due to external light.

[High-Speed Brightness Adjustment Based on Gradient in Amount of Light]

Light is emitted from each of the four near infrared LED so that the amount of light changes with the difference in location among the four near infrared LEDs. Thereby, the transmission brightness changes with the difference in location. From the thus-obtained transmission brightnesses different from one another, one transmission brightness most suitable for obtaining a target brightness is selected so that an amount of light emitted from each near infrared LED is set up for obtaining the target brightness. Thus, the amount of light can be controlled within a time used to capture one image.

Figure 6:
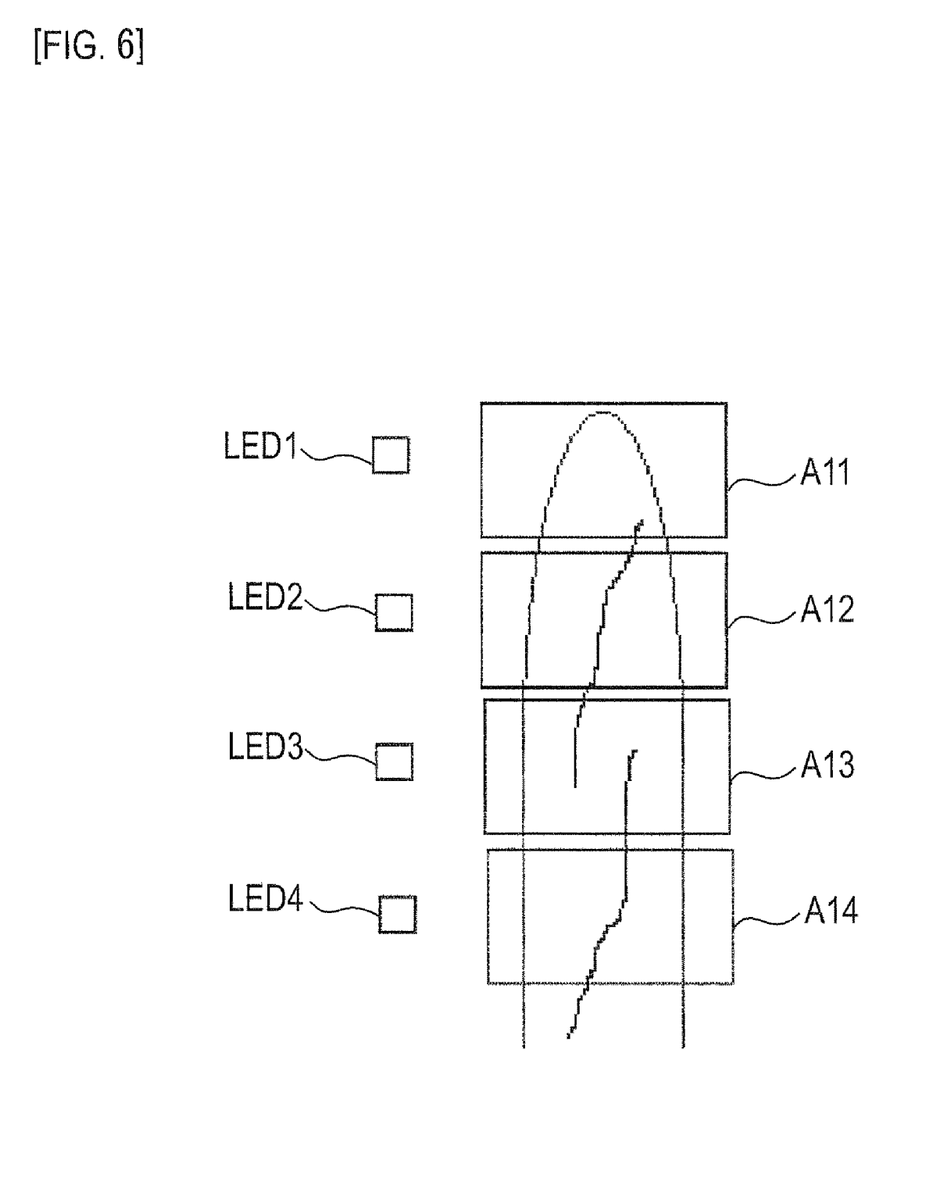
FIG. 6 is a diagram showing a relationship between a location of an LED and an emitted area according to the embodiment of the present invention.

FIG. 6 shows a relationship between the locations of the LEDs and the respective emitted areas. Using FIG. 6, descriptions will be provided for how the amount of light emitted from each LED is adjusted on the basis of the gradient in the amount of light. For example, the amount of light emitted from the LED 1 is set smaller than the amount of light emitted from the LED 2, which is set smaller than the amount of light emitted from the LED 3, which is set smaller than the amount of light emitted from the LED 4. In addition, the area illuminated by light from the LED 1 is denoted by A11; the area illuminated by light from the LED 2 is denoted by A12; the area illuminated by light from the LED 3 is denoted by A13; and the area illuminated by light from the LED 4 is denoted by A14. Here, let us assume that the transmission brightness of the area A12 is the closest to the target brightness among the transmission brightnesses of the respective areas A11, A12, A13 and A14. In such a case, the amount of light emitted from each of the LED 1, the LED 3 and the LED 4 is set equal to the amount of light emitted from the LED 2.

[Selection from Multiple Images]

Although the brightness is automatically adjusted in the above-described manner when an image is captured, no optimal image may be acquired, in some cases, due to individual difference or environmental change. For example, some finger, which is thick enough to decrease the transmittance of light, makes it difficult for its vein to be photographed under a standard brightness. In addition, some other finger, which is slender with a slender vein, makes the image of the vein indistinct or vague under the standard brightness because the vein allows some portion of light to reach the back of the vein.

In these cases, images are captured beyond a minimum number of images needed to reproduce a vein pattern with the range of brightness adjustment (range of the amount of light)

being expanded, and an optimal image is selected from the captured images. This scheme makes it possible to reproduce a vein pattern which less deviates from the actual vein pattern.

Once images are captured beyond a minimum number of images needed to reproduce a vein pattern, an optimal image is selected from the captured images in the following manner.

(1) First of all, a process numbered (2) and ensuing processes are applied to each of the images which are captured beyond a minimum number of images needed to reproduce a vein pattern.

(2) A variance in brightness among given areas (each constituting multiple points) is calculated.

For example, in a 100×256 image area, a brightness average of each given 64 points is calculated. In this respect, each given 64 points include a point at coordinates (x, y) to a point at coordinates (x+7, y+7), where (x,y)=(16,25), (88,25), (160, 25), (232,25), (16,50), (88,50), (160,50), (232,50). Thus, 8 brightness averages are obtained. Subsequently, the variance is calculated from the 8 brightness averages in the following manner.

(2-1) Specifically, an average brightness Lm1 is calculated for 64 points including a point at coordinate (16,25) to a point at coordinates (16+7,25+7), i.e., (16,25), (16,26), (16,27), (16,28), (16,29), (16,30), (16,31), (16,32), (17,25), . . . , (17,32), (18,25), . . . , (18,32), (19,25), . . . , (19,32), (20,25), . . . , (20,32), (21,25), . . . , (21,32), (22, 25), . . . , (22,32), (23,25), . . . , (23,32).

(2-2) Similarly, for each set of coordinates (x,y) where (x,y)=(88,25), (160,25), (232,25), (16,50), (88,50), (160, 50), (232, 50), a brightness average is calculated for the 64 points including a point at coordinate (x,y) to a point at coordinate (x+7,y+7). Thus, the brightness averages Lm2 to Lm8 are obtained.

(2-3) The variance among the brightness averages Lm1 to Lm8 is defined as follows. The variance is used as a criterion for showing how the pixel values are dispersed.

Average $M = (Lm1 + Lm2 + \ldots + Lm8)/8$.

Variance $= \{(Lm1-M)^2 + (Lm2-M)^2 + \ldots + (Lm8-M)^2\}/8$.

(3) The foregoing process is applied to all the images.

(4) An image whose variance is the largest among the variances of the respective images is selected. Subsequently, some multiple images captured using amounts of light, which are larger than an amount of light used to capture the image having the largest variance, and other multiple images captured using amounts of light, which are smaller than the amount of light used to capture the image having the largest variance, are selected.

For example, let us assume that 20 images are captured with an amount of light being changed. In this case, suppose that an amount of light used to capture an image is gradually increased so that: an amount of light used to capture an image 01 is the smallest; an amount of light used to capture an image 02 is larger than the amount light used to capture the image 01; an amount of light used to capture an image 03 is larger than the amount light used to capture the image 02; an amount of light used to capture an image 04 is larger than the amount of light used to capture the image 03; . . . ; and an amount of light used to capture an image 20 is the largest. In addition, assume that when the variance is calculated for each of the 20 images, the variance of the image 07 is the largest. In such a case, the image 07, 3 images captured using amounts of light, which are immediately larger than the amount of light used to capture the image 07, and other 3 images captured using amounts of light, which are immediately smaller than the amount of light used to capture the image 07, are selected. In other words, the image 04, the image 05, the image 06, the image 07, the image 08, the image 09 and the image 10 are selected.

[Updating of Dictionary Database]

In the case of the first and second embodiments, for each finger, multiple vein patterns are stored in the memory 7; and each time a finger is evaluated in terms of its authenticity, the vein pattern of the finger is compared with stored multiple vein patterns. For example, when it is evaluated whether or not a vein pattern is that of Mr. A, the evaluation is achieved on the basis of the correlation coefficient which is calculated between the vein pattern and each of the stored multiple vein patterns of Mr. A with the vein pattern being compared with each stored vein pattern. It is ideal that the multiple vein patterns should be different from one another to a reasonable extent.

When environmental conditions in which multiple vein patterns are registered are different from environmental conditions in which a vein pattern is evaluated for authenticity (such as season, age, apparatus placement location), even if the vain pattern is judged as resembling any one of the stored vein patterns, the authentication score (synonymous with the correlation coefficient obtained by dividing the value of cross-correlation by the value of autocorrelation) concerning some vein pattern may be low. In such a case, it is desirable that: the vein pattern which has just been scanned should be stored in the memory 7 in exchange for deleting a vein pattern which has the lowest authentication score among the vein patterns stored in the memory 7.

[Adjustment to Physical Growth on the Basis of Multiple Pattern Database]

In a case where a subject of evaluation is a child, as time passes after an initial registration, the child's growth changes the size of the finger. The change in the size of the finger is likely to subtly change the characteristics of the vein pattern of the finger. If the vein pattern database is not updated despite the change, the authentication score may decrease gradually. If the database is updated each time a predetermined condition is satisfied, the authentication performance can be kept optimal.

[Adjustment to Displacement on the Basis of Multiple Pattern Database]

Because environmental conditions in which authentication is evaluated are different from environmental conditions in which an initial registration is made, a habitual manner of placing the finger on the authentication apparatus for the evaluation is likely to become different from a manner of placing the finger on the apparatus during the registration. In addition, as the number of times the authentication apparatus is used increase, a habitual manner of placing the finger on the apparatus is likely to change gradually. When the habitual manner of placing the finger on the apparatus changes too much, the authentication score is likely to decrease to an extent that the vein pattern needs to be registered again. If the database is updated each time a predetermined condition is satisfied, the authentication performance can be kept optimal.

Descriptions will be provided for an example of how the database is updated.

(1) Multiple patterns are registered during an initial registration. (2) When authentication is carried out, a matching is performed for all patterns so as to calculate the authentication score (synonymous with the correlation coefficient obtained by dividing the value of cross-correlation by the value of autocorrelation). (3) When a registered pattern has a high score, the registered pattern is judged as suitable for the present environmental conditions and the present habitual manner of placing the finger on the apparatus. (4) For each registered pattern, the number of times the registered pattern is judged as suitable is recorded. (5) When a particular pattern is not judged as suitable at all, or when the number of times a particular pattern is judged as suitable is extremely small, the pattern is deleted from the memory 7, and the new vein pattern just scanned by the camera 8 is instead stored in the memory 7. In other words, as part of the set of data on the registration, a new set of data on the evaluation is stored in the memory 7.

For example, let us assume that: with regard to a finger of Mr. A, 3 vein patterns (patterns P11, P12 and P13) are registered; and when Mr. A places the same finger on the authentication apparatus, a vein pattern P14 of the finger of Mr. A is scanned by the camera 8. When the authentication score of the vein pattern P11 is smaller than the authentication score of the vein pattern P12 which is smaller than the authentication score of the vein pattern P13, the number of times the vein pattern 13 is judged as suitable increases by one.

Suppose that: thereafter, the process of scanning a vein pattern of the same finger of Mr. A, which is placed on the authentication apparatus, is repeated 9 times using the camera 8; the number of times the vein pattern P13 is judged as suitable increases by 4; the number of times the vein pattern P12 is judged as suitable increases by 5; and the number of times the vein pattern P11 is judged as suitable does not increase at all.

In this case, the vein pattern P11 is deleted from the memory 7, and the new vein pattern scanned by the camera 8 is instead stored in the memory 7.

If, however, a pattern which is not judged as suitable has a high score, it is desirable that the database should be not updated.

The invention claimed is:

1. An authentication apparatus comprising:
    a light source that emits an infrared light beam onto a finger;
    image pick-up means that picks up an image of the finger by using a transmitted light beam, and thus outputs an image signal;
    low-frequency brightness component extracting means that extracts a low-frequency brightness component signal from the image signal by using a low-pass filter;
    middle-frequency brightness component extracting means that extracts a middle-frequency brightness component signal from the image signal by using a middle-pass filter;
    correction means that corrects the middle-frequency brightness component signal by using the low-frequency brightness component signal;
    quaternary-value converting means that converts the corrected middle-frequency brightness component signal into quaternary values such that the quaternary values are distributed at a predetermined ratio;
    storage means that stores a quaternary-valued image obtained from the quaternary-value conversion by the quaternary-value converting means;
    correlation coefficient calculating means that calculates a correlation coefficient between a quaternary-valued evaluation image as an object of evaluation and a quaternary-valued registered image by using a pattern matching method based on a normalized correlation method, the quaternary-valued evaluation image obtained from the quaternary-value conversion by the quaternary-value converting means, the quaternary-valued registered image being beforehand stored in the storage means; and
    judgment means that judges whether or not the quaternary-valued evaluation image and the quaternary-valued registered image are images picked up from the same finger on a basis of the correlation coefficient which is calculated by the correlation coefficient calculating means.

2. The authentication apparatus according to claim 1, wherein the correlation coefficient calculating means calculates the correlation coefficient by using the following formula 1, $$\text{correlation coefficients} = F/G \qquad \text{[Formula 1]}$$

where: F represents a value of cross-correlation between the evaluation image and the registered image, and is defined as $F=\Sigma(I \times T)$; G represents a value of autocorrelation of the registered image, and is defined as $G=\Sigma(T \times T)$; I denotes a brightness of the evaluation image; and T denotes a brightness of the registered image.

3. The authentication apparatus according to claim 2,
    further comprising quaternary-valued reduced image generating means that generates a quaternary-valued reduced image by convolving a plurality of cells included in the quaternary-valued image obtained from the quaternary-value conversion by the quaternary-value converting means, wherein:
    the correlation coefficient calculating means calculates a primary correlation coefficient between a quaternary-valued reduced evaluation image generated from the quaternary-valued evaluation image, and a quaternary-valued reduced registered image beforehand stored in the storage means, by using the pattern matching method based on the normalized correlation method; and
    only when the primary correlation coefficient is not less than a predetermined value, the correlation coefficient calculating means calculates the correlation coefficient between the quaternary-valued evaluation image associated with the quaternary-valued reduced evaluation image, and the quaternary-valued registered image associated with the quaternary-valued reduced registered image, by using the pattern matching method based on the normalized correlation method.

4. The authentication apparatus according to any one of claim 2, further comprising a high-frequency brightness component extracting means that extracts a high-frequency brightness component signal from the image signal by using a high-pass filter, wherein:
    the correction means corrects the middle-frequency brightness component signal and the high-frequency brightness component signal by using the low-frequency brightness component signal;
    the quaternary-value converting means converts the corrected middle-frequency brightness component signal into quaternary values such that the quaternary values are distributed at a first predetermined ratio, and converts the corrected high-frequency brightness component signal into quaternary values such that the quaternary values are distributed at a second predetermined ratio;
    the correlation coefficient calculating means calculates (1) a middle-frequency correlation coefficient between a quaternary-valued middle-frequency evaluation image obtained from the middle-frequency brightness component signal, and a quaternary-valued middle-frequency registered image beforehand stored, and (2) a high-frequency correlation coefficient between a quaternary-valued high-frequency evaluation image obtained from the high-frequency brightness component signal, and a quaternary-valued high-frequency registered image beforehand stored; and on the basis of the middle-frequency correlation coefficient and the high-frequency correlation coefficient, the judgment means judges whether or not the quaternary-valued middle-frequency evaluation image and the quaternary-valued middle-frequency registered image are images picked up from the same finger, and whether or not the quaternary-valued high-frequency evaluation image and the quaternary-valued high-frequency registered image are images picked up from the same finger.

5. The authentication apparatus according to claim 1, further comprising quaternary-valued reduced image generating means that generates a quaternary-valued reduced image by convolving a plurality of cells included in the quaternary-valued image obtained from the quaternary-value conversion by the quaternary-value converting means, wherein:

the correlation coefficient calculating means calculates a primary correlation coefficient between a quaternary-valued reduced evaluation image generated from the quaternary-valued evaluation image, and a quaternary-valued reduced registered image beforehand stored in the storage means, by using the pattern matching method based on the normalized correlation method; and only when the primary correlation coefficient is not less than a predetermined value, the correlation coefficient calculating means calculates the correlation coefficient between the quaternary-valued evaluation image associated with the quaternary-valued reduced evaluation image, and the quaternary-valued registered image associated with the quaternary-valued reduced registered image, by using the pattern matching method based on the normalized correlation method.

6. The authentication apparatus according to any one of claim 5, further comprising a high-frequency brightness component extracting means that extracts a high-frequency brightness component signal from the image signal by using a high-pass filter, wherein:

the correction means corrects the middle-frequency brightness component signal and the high-frequency brightness component signal by using the low-frequency brightness component signal;

the quaternary-value converting means converts the corrected middle-frequency brightness component signal into quaternary values such that the quaternary values are distributed at a first predetermined ratio, and converts the corrected high-frequency brightness component signal into quaternary values such that the quaternary values are distributed at a second predetermined ratio;

the correlation coefficient calculating means calculates (1) a middle-frequency correlation coefficient between a quaternary-valued middle-frequency evaluation image obtained from the middle-frequency brightness component signal, and a quaternary-valued middle-frequency registered image beforehand stored, and (2) a high-frequency correlation coefficient between a quaternary-valued high-frequency evaluation image obtained from the high-frequency brightness component signal, and a quaternary-valued high-frequency registered image beforehand stored; and on the basis of the middle-frequency correlation coefficient and the high-frequency correlation coefficient, the judgment means judges whether or not the quaternary-valued middle-frequency evaluation image and the quaternary-valued middle-frequency registered image are images picked up from the same finger, and whether or not the quaternary-valued high-frequency evaluation image and the quaternary-valued high-frequency registered image are images picked up from the same finger.

7. The authentication apparatus according to any one of claim 1, further comprising a high-frequency brightness component extracting means that extracts a high-frequency brightness component signal from the image signal by using a high-pass filter, wherein:

the correction means corrects the middle-frequency brightness component signal and the high-frequency brightness component signal by using the low-frequency brightness component signal;

the quaternary-value converting means converts the corrected middle-frequency brightness component signal into quaternary values such that the quaternary values are distributed at a first predetermined ratio, and converts the corrected high-frequency brightness component signal into quaternary values such that the quaternary values are distributed at a second predetermined ratio;

the correlation coefficient calculating means calculates (1) a middle-frequency correlation coefficient between a quaternary-valued middle-frequency evaluation image obtained from the middle-frequency brightness component signal, and a quaternary-valued middle-frequency registered image beforehand stored, and (2) a high-frequency correlation coefficient between a quaternary-valued high-frequency evaluation image obtained from the high-frequency brightness component signal, and a quaternary-valued high-frequency registered image beforehand stored; and on the basis of the middle-frequency correlation coefficient and the high-frequency correlation coefficient, the judgment means judges whether or not the quaternary-valued middle-frequency evaluation image and the quaternary-valued middle-frequency registered image are images picked up from the same finger, and whether or not the quaternary-valued high-frequency evaluation image and the quaternary-valued high-frequency registered image are images picked up from the same finger.

8. An authentication method comprising the steps of:

emitting an infrared light beam onto a finger;

picking up an image of the finger by using a transmitted light beam, and thus outputting an image signal;

extracting a low-frequency brightness component signal from the image signal by using a low-pass filter;

extracting a middle-frequency brightness component signal from the image signal by using a middle-pass filter;

correcting the middle-frequency brightness component signal by using the low-frequency brightness component signal;

converting the corrected middle-frequency brightness component signal into quaternary values such that the quaternary values are distributed at a predetermined ratio;

storing a quaternary-valued image obtained by from the quaternary value conversion;

calculating a correlation coefficient between a quaternary-valued evaluation image as an object of evaluation, and a quaternary-valued registered image by using a pattern matching method based on a normalized correlation method, the quaternary-valued evaluation image obtained by from the quaternary value conversion, the quaternary-valued registered image being beforehand stored; and judging whether or not the quaternary-valued evaluation image and the quaternary-valued registered image are images picked up from the same finger on a basis of the correlation coefficient.

* * * * *